United States Patent [19]

Ichihashi et al.

[11] Patent Number: 4,838,683

[45] Date of Patent: Jun. 13, 1989

[54] OPHTHALMIC MEASURING METHOD AND APPARATUS

[75] Inventors: Tadashi Ichihashi; Masunori Kawamura, both of Hino, Japan

[73] Assignee: Kowa Company Ltd., Aichi, Japan

[21] Appl. No.: 51,666

[22] Filed: May 18, 1987

[30] Foreign Application Priority Data

May 19, 1986 [JP] Japan .................................. 61-112516
May 28, 1986 [JP] Japan .................................. 61-121126

[51] Int. Cl.$^4$ .............................................. A61B 3/10
[52] U.S. Cl. ...................................... 351/221; 128/633
[58] Field of Search ............... 351/205, 211, 221, 215, 351/246; 128/633, 745

[56] References Cited

U.S. PATENT DOCUMENTS 4,208,107  6/1980  Oharek .................................. 351/215
4,702,576 10/1987  Magnante ............................. 351/221

Primary Examiner—Rodney B. Bovernick
Assistant Examiner—P. M. Dzierzynski
Attorney, Agent, or Firm—Bruce L. Adams; Van C. Wilks

[57] ABSTRACT

An ophthalmic measuring method and apparatus according to the present invention are provided for the purpose of measuring the state of microparticles in the aqueous chamber of an eye to be examined which is irradiated with a laser beam to detect the scattering characteristics in the aqueous chamber of the eye. A laser beam with a predetermined wavelength is projected into the aqueous chamber of the eye. Light scattered from the aqueous chamber is received with or without a linear polarizer and evaluated in terms of the changes between the scattering characteristics with or without the linear polarizer in order to measure the number or concentration of the microparticles present in the aqueous chamber for the purpose of detecting ophthalmic diseases.

8 Claims, 6 Drawing Sheets

FIG. 1

| STATE OF INFLAMMATION | NO SCANNING WITHOUT POLARIZER | SCANNING | |
|---|---|---|---|
| | | WITH POLARIZER | WITHOUT POLARIZER |
| FLARES ONLY | MOST SUITABLE | UNSUITABLE | ACCEPTABLE |
| CELLS ONLY SMALL NUMBER | UNSUITABLE | ACCEPTABLE | MOST SUITABLE |
| CELLS ONLY LARGE NUMBER | UNSUITABLE | MOST SUITABLE | ACCEPTABLE |
| FLARES AND CELLS (SMALL NUMBERS) | UNSUITABLE | UNSUITABLE | ACCEPTABLE |
| | | MOST SUITABLE | |
| FLARES AND CELLS (LARGE NUMBERS) | UNSUITABLE | UNSUITABLE | UNSUITABLE |
| | | MOST SUITABLE | |

OPHTHALMIC MEASURING METHOD AND APPARATUS

BACKGROUND OF THE INVENTION

1. Field of the Invention

This invention relates to an ophthalmic measuring method and apparatus, and more particularly to a method and apparatus for measuring the state of fine particles in the aqueous chamber of a patient's eye which is being examined and which is irradiated with a laser beam to detect the scattering characteristics in the aqueous chamber of the eye.

2. Description of the Prior Art

Measurements of the plasma protein concentration and of the blood corpuscle count and other cell counts inside the aqueous chamber are extremely important in diagnosing states of inflammation inside the aqueous chamber, both endogenous or exogenous.

The plasma protein concentration in the aqueous chamber, as well as the state of micro-particles such as blood corpuscles there, was determined in most cases in the past by means of visual inspections using a slit-lamp microscope.

In the aforesaid method of the past, the criteria for judgment were quite diverse on account of the individual differences between observers, and the data obtained by this method were lacking in reliability.

In addition to the aforesaid methods using subjective observations, other indirect methods of measuring the plasma proteins have also been proposed. In these methods, a fluorescent material such as fluorescein is injected into the body intravenously, and the fluorescent intensity of the fluorescein flowing into the aqueous chamber is measured. However, these methods impose a heavy physical burden on the patient and are problematic from the clinical viewpoint.

SUMMARY OF THE INVENTION

Therefore, the purpose of this invention is to provide an ophthalmic measuring method and apparatus whereby the microparticle count inside the aqueous chamber can be measured quantitatively.

The ophthalmic measuring method of the present invention is one in which the state of microparticles in the aqueous chamber of a patient's eye being examined is determined by irradiating it with a laser beam in order to detect the scattering characteristics in the aqueous chamber of the eye. The steps include one in which a laser beam with a predetermined wavelength is projected into the aqueous chamber; one in which the light scattered from the aqueous chamber is received with or without a linear polarizer; and one in which the differences between the scattering characteristics with and without said linear polarizer are evaluated in order to measure the number or concentration of the microparticles present in the aqueous chamber.

According to the preferred embodiment, the microparticles are plasma proteins or blood corpuscles, and the laser beam is scanned when the aqueous chamber contains more blood corpuscles than plasma proteins but is not scanned when the aqueous chamber contains only plasma proteins.

The aforesaid configuration makes it possible to analyze quantitatively the quantity and type of the microparticles present in the aqueous chamber in accordance with the polarization characteristics of the light scattered by the microparticles in the aqueous chamber.

BRIEF DESCRIPTION OF THE DRAWINGS

The purposes and features of the present invention will become more apparent from a consideration of the following detailed description taken in conjunction with the accompanying drawings in which:

FIGS. 7 (A) and (B) are an oblique drawing and a block diagram showing the configuration of the apparatus for embodying the method of this invention for measuring microparticles.

FIG. 8 (A) and (B) are block diagrams showing in greater detail parts of the circuitry of FIG. 7 (B)

DETAILED DESCRIPTION OF PREFERRED EMBODIMENTS

This invention is described in detail below on the basis of the preferred embodiments illustrated in the drawings.

In this embodiment, the aqueous chamber of a patient's eye is irradiated with laser light, the scattered light is detected by a photoelectric converter, the number of microparticles in the aqueous chamber, consisting of plasma proteins or cells such as blood corpuscles, is measured by means of digital processing, and this makes it possible to obtain an objective understanding of the conditions inside the aqueous body. The basic principles of the measuring method of this embodiment are explained below.

According to Mie's scattering theory, when microparticles are irradiated from the horizontal direction with unpolarized light, the characteristics of the light scattered from the microparticles may be explained in the following way.

If the microparticles subjected to irradiation are equal in size to or smaller than the wavelength of the irradiated light, the scattered light will consist almost entirely of linear polarized light in the vertical direction, when observed within a horizontal plane from a 90-degree angle with respect to the incident direction of the irradiated light.

If, on the other hand, the microparticles are larger than the wavelength of the irradiated light, they will contain horizontally polarized components in addition to the vertically polarized components. That is, in this case the scattered light will not consist entirely of linear polarized light.

Therefore, if this theory is applied, in the diagnosis of inflammation in the aqueous chamber of a patient's eye, to the measurement of microparticles inside the aqueous chamber, it will be possible to use laser light, which has a high luminance and high convergence characteristics, as the light source, and to set its wavelength at a value approximately equal to the size of the microparticles of the protein components, i.e. to the visible and near-infrared regions. This is desirable because the differences in the polarization characteristics of the scattered light produced by the plasma proteins (microparticles on the submicron order) and that produced by blood corpuscles and the like (microparticles measuring several microns or larger) are utilized in the diagnosis. It is possible, for example, to use He-Cd lasers (442 nm), Ar+ lasers (488 nm), He-Ne lasers (544, 633 nm) or semiconductor lasers (approximately 780 nm).

A linear polarizer which filters the scattered light may be used to detect independently the vertically and horizontally polarized components of the light scattered in the aqueous chamber.

For the sake of simplification, let us here call the plasma proteins "flares" and blood corpuscles "cells." According to the polarization theory cited above, when irradiated with laser light having wavelengths such as those mentioned, the light scattered from the flares, which are equal in size to or smaller than the wavelength, will be 10 vertically polarized, while the light scattered by the cells will include both vertical and horizontal components.

Therefore, if a polarizer which will allow only the horizontally polarized components to pass through is located before the photoelectric converter which detects the scattered light, the light scattered from the flares will be cut out by this polarizer, since the light scattered from the flares consists solely of vertically polarized components. On the other hand, since the light scattered from the cells contains horizontally polarized components, only the horizontally polarized components from the cells will be admitted into the photoelectric converter. That is, in this case, the output of the photoelectric converter will contain only information about the light scattered from the cells.

If the polarizer is removed from its location before the photoelectric converter, the output of the photoelectric converter will contain information concerning both the light scattered from the flares and that scattered from the cells.

Figure 1:
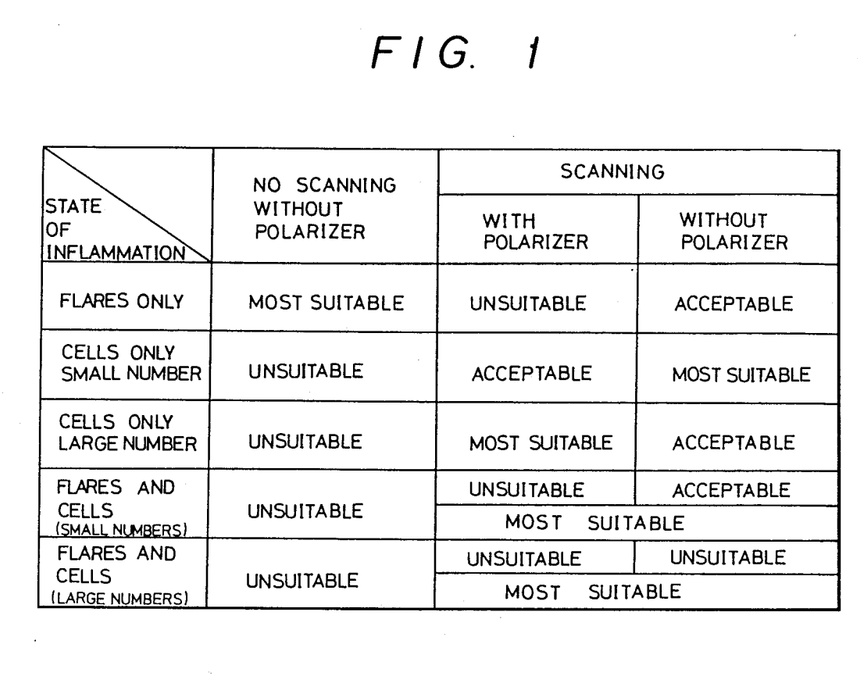
FIG. 1 is an explanatory drawing of the presence or absence of a polarizer and whether scanning is suitable or not.

When one is finding the scattering characteristics by laser irradiation, it is conceivable to adopt a system of irradiation such as that shown in FIG. 1, in which the characteristics of the flares and cells are utilized in addition to the aforesaid presence and absence of the polarizer. FIG. 1 indicates the suitability for various types of particles which one wishes to measure.

In FIG. 1, the laser beam is scanned in cases where either flares alone or cells alone are to be measured. This is done in order to increase the measured volume and to make it possible to measure more accurately the number of cells present in the aqueous chamber. On the other hand, since flares are distributed uniformly throughout the aqueous chamber, it is believed that it is not necessary to scan the beam in cases where one needs to know only the flare concentration.

When both flares and cells are present and it is desired to measure both of them quantitatively, the beam will be scanned, and measurements will be taken several times, inserting and removing the polarizer.

Next let us explain the method for digitally processing the output of the photoelectric converter and calculating the flare concentration and the cell count.

Figure 2:
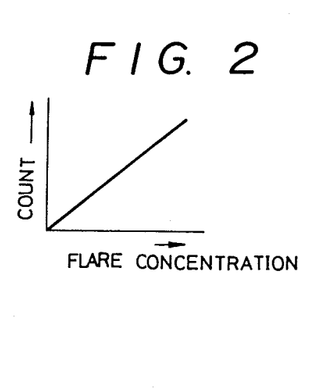
FIGS. 2–6 are each graphs explaining the method of this invention for measuring microparticles inside the aqueous chamber.

First of all, if flares alone are to be measured, the mean values of the detected pulse counts which are output from the photoelectric converter at specific time intervals are calculated, and the flare concentration is calculated by substituting the mean values in a known proportional equation for the flare concentrations and pulse counts. FIG. 2 shows the proportional relationship used in this case.

The following processing is performed in cases where only a few cells are present within the measured volume in the aqueous chamber and it is desired to know their number. In these cases, the output pulse of the photoelectric converter per unit time may be plotted in a time series as shown in FIG. 3.

Figure 3:
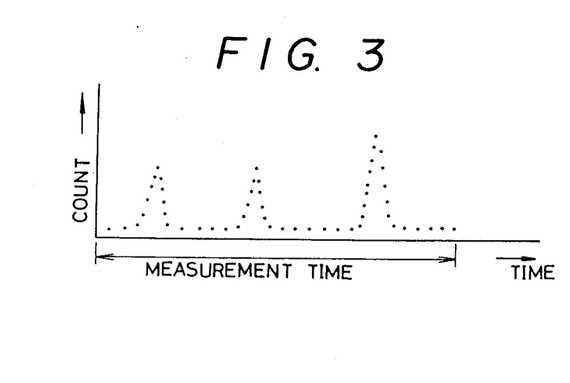

If, for example, the unit which is scanned has a volume of 1 mm$^3$ inside the aqueous chamber, it will be possible to find the quantity of cells within the unit of volume measured by counting the number of peaks in FIG. 3 which occur during the time of measurement.

Figure 4:
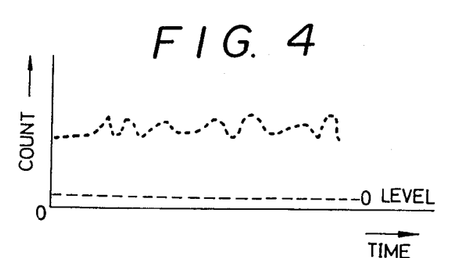

In cases where a number of cells are always present in the volume measured, the pulse counts may be plotted in a time series in the same way, as is shown in FIG. 4. In cases such as this where a number of cells are present, counting the number of peaks will not give a measured value of the number of cells. However, no matter how many cells are present within the volume measured, since there is a predetermined scattering intensity per cell, there will be a proportional relationship such as that shown in FIG. 5 between the cell count and the scattering intensity (the count value). Consequently, analysis in this region can be performed by calculating the mean of the count values per time units and then calculating the number of cells by substituting the mean in a known proportional equation for the cell counts and the count value.

Figures 5, 6:
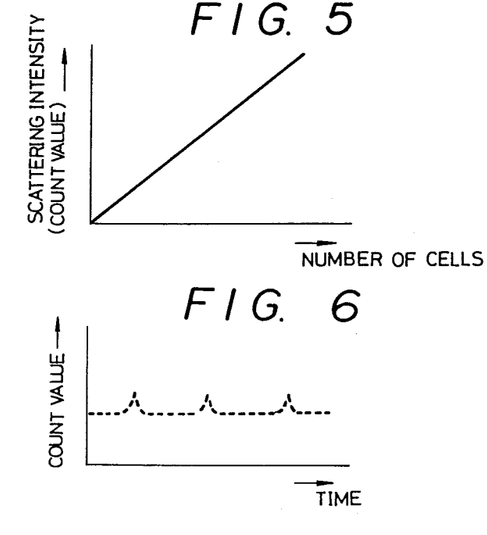

FIG. 6 shows a similar time-series plot of the output of the photoelectric converter in cases where small numbers of both flares and cells are present. The base areas under the peaks are higher than in FIG. 3 because of the light scattered by the flares. Analysis in this case is performed by first counting the number of peaks to measure the number of cells by the same technique as that described above. Then the flare concentration is determined on the basis of the proportional relationship in FIG. 2 by means of the count value per unit time excluding that forming the peaks.

However, when there is an extremely high flare concentration, the scattering intensity of the flares will cancel out that from the cells, and peaks due to the cells will not appear when the count values per unit time are plotted in a time sequence. In such cases, the flare components can be cut out by inserting a linear polarizer and taking measurements, in accordance with the theory mentioned above. This makes it possible to obtain measurements in accordance with the proportional equation. The flare concentration is determined on the basis of the data obtained when the linear polarizer is removed.

In cases where large numbers of both flares and cells are present, as was mentioned above, the count value changes in accordance with the number of cells regardless of the flare concentration. Since the count value due to the light scattered by the flares will also be added to the count value, the cell count is determined by the aforesaid method, in which the cell components are measured through a linear polarizer in order to eliminate the flare components. After this, the data obtained after the linear polarizer is removed may be used in calculations to remove the influence of the cells, and the final flare concentration may be determined in this way.

Next let us describe in detail an apparatus for implementing the aforesaid method.

Figure 7A:
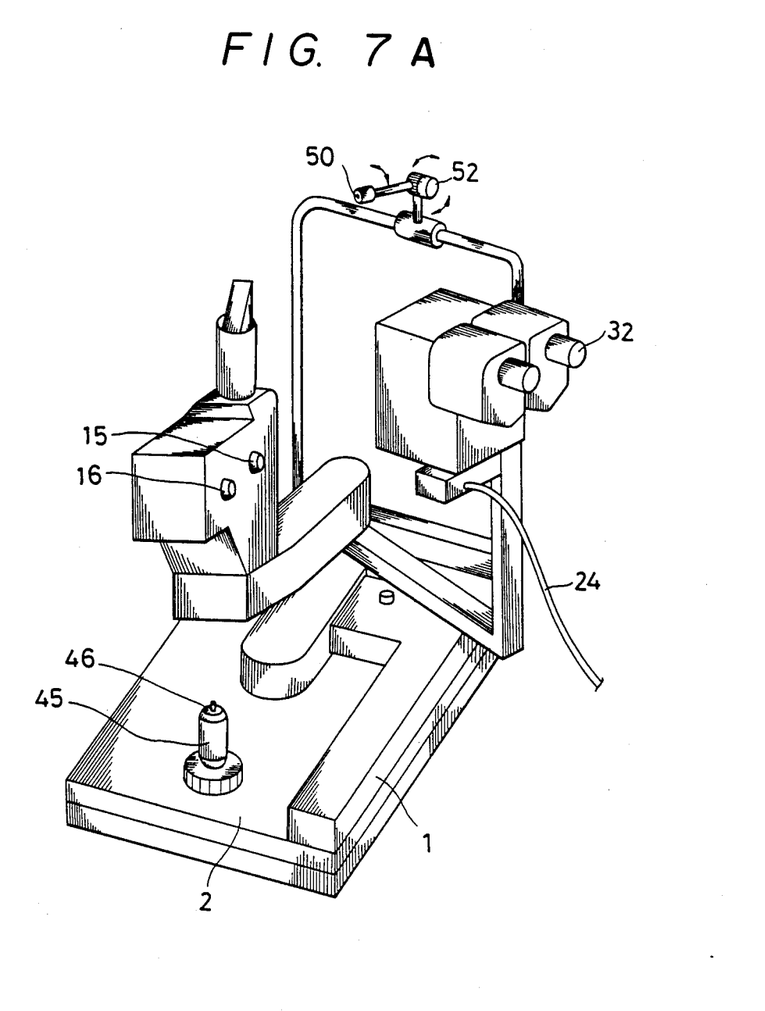
Figure 7B:
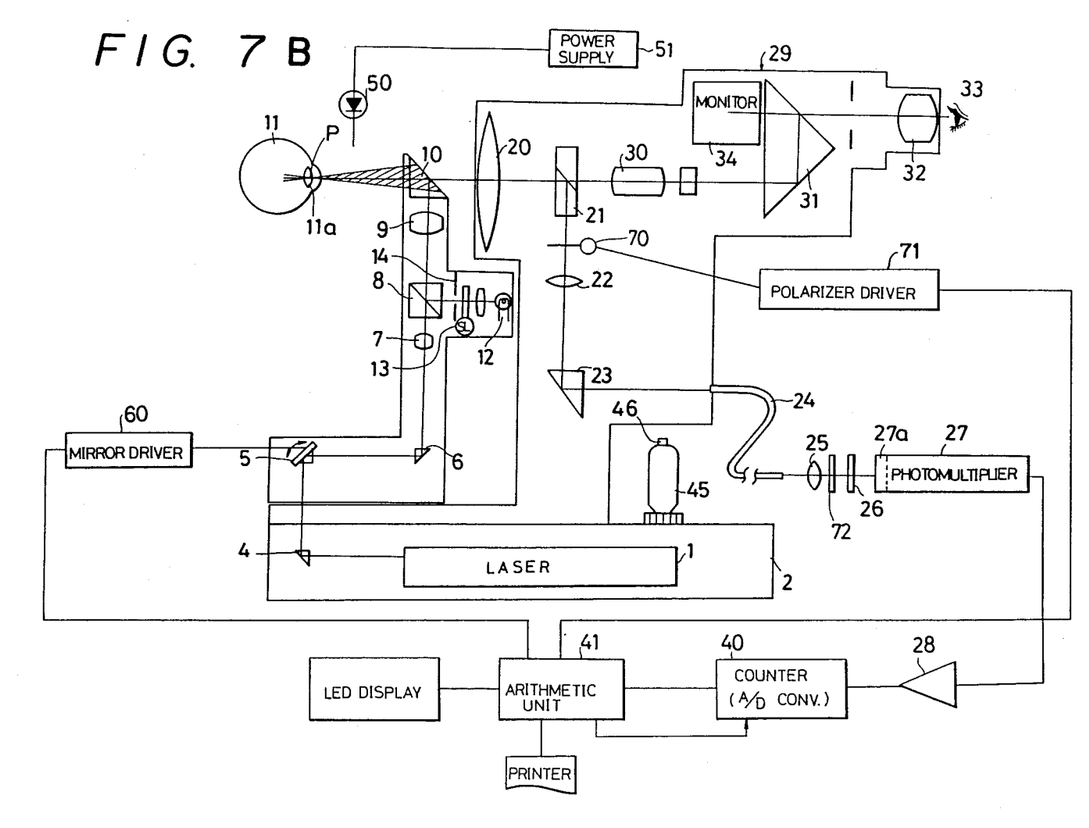

FIG. 7 (A) and (B) show the schematic configuration of an ophthalmic measuring apparatus based on this invention. Symbol 1 in these figures represents a laser light source of the helium-neon or similar type. This light source 1 is located on a table 2. The light from the light source 1 passes through a prism 4, lens 7, beam splitter 8, lens 9 and prism 10 and is focused so as to be concentrated at a single point in the aqueous chamber 11a of the patient's eye 11.

This laser light source is provided with a light source 12 for slit observation. The light from this light source 12 passes through a slit-light shutter 13 and a slit 14 and is focused via a beam splitter 8, lens 9 and prism 10 as a slit image on the aqueous chamber 11a. Since the light from the aforesaid laser light source is focused in a point shape, this slit image is for the purpose of providing illumination around it so that the location of the point image can be ascertained easily.

The width and length of the slit 14 can be changed by means of the slit width adjustment knob 15 and the slit length adjustment knob 16.

A portion of the laser light scattered from the measuring point in the aqueous chamber 11a passes through the objective 20 in the detector 29 and is divided by the beam splitter 21. Another portion of it passes through the polarizing filter 70, lens 22, prism 23, optical fiber 24, lens 25, interference filter 72 and photomultiplier shutter 26 and is admitted into the photomultiplier 27, which functions as a photoelectric converter. The other scattered light which is divided by the beam splitter 21 can be observed through the variable-power lens 30, prisms 31, monitor 34 and eyepiece 32.

The output of the photomultiplier 27 is input through an amplifier 28 into a counter 40 (or an A/D converter), and the scattered light intensity detected by the photomultiplier 27 is measured as the number of photons (it is converted into a digital value if an A/D converter is used).

The output of this counter 40 or converter is input into an arithmetic unit 41, which calculates the plasma protein concentration and the number of cells in the aqueous chamber. The results are displayed on an LED display 47. The calculation results may also be output with a printer 48 or the like.

In this invention, there is a fixating lamp 50 consisting of LEDs or the like. Its power is supplied from a power source 51, and it is located in a position where the patient can fix his or her vision on it. The color of this fixating lamp 50 is selected so as to be different from the color of the laser light source 1. That is, if the laser is red, a color such as green is selected as the color of the fixating lamp 50. This fixating lamp 50 can be rotated by means of a linking mechanism 52 or the like in order to adjust its position to be convenient to the patient.

A push-button 46 is also provided on the table 2, and an input device such as a joystick 45 is also provided. The slit-light shutter 13 and photomultiplier shutter 26 can each be inserted into or removed from the optical system by operating the joystick.

The linear polarizer 70 can also be inserted or removed as necessary by means of a linear polarizer driving circuit 71 connected to the arithmetic unit 41.

When making measurements, the light source 12 is first turned on, and the slight image of the slit 14 is focused on the part of the aqueous chamber 11a including the measuring point P. Next light from the laser light source 1 is passed through the optical system and concentrated on the measuring point P.

A portion of the light scattered at the measuring point P is aimed towards the technician 33 by the beam splitter 21. As soon as it is observed, it is admitted into the photomultiplier 27 through the optical system including the lens 22, prism 23 and optical fiber 24. This photomultiplier detects the intensity of the light scattered by the plasma proteins and cells in the aqueous chamber 11a; its intensity is measured as the number of photons. If an A/D converter is used, the output of the photomultiplier 27 is converted from an analog to a digital value.

After having been converted as described above into a pulse train or a digital quantity, the data are input into the arithmetic unit 41, which calculates the number of large scattered microparticles such as cells and the plasma protein concentration in the aqueous chamber.

There is a movable mirror 5 which is oscillated by a mirror driving circuit 60 connected to the arithmetic unit 41. This makes it possible to scan the laser light and to move the point of laser light produced inside the aqueous chamber by the laser light source. Since the measuring point is moved by this means in order to detect the blood corpuscles which are present in any given place, it is possible to make measurements over a broad range and to improve the precision of detection.

Figure 8A:
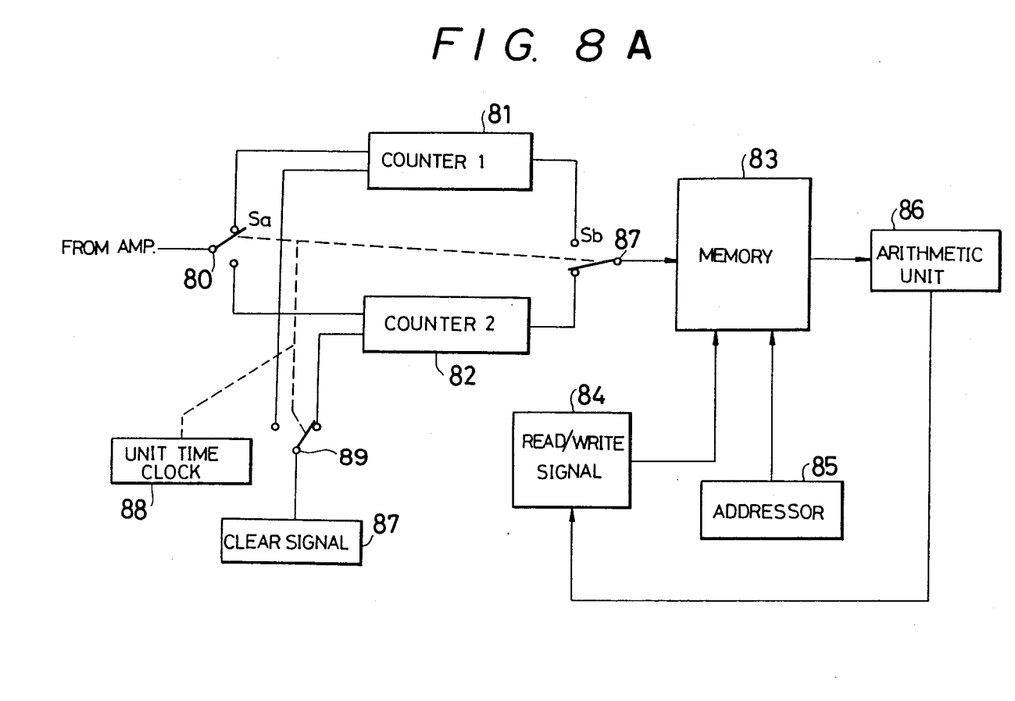
Figure 8B:
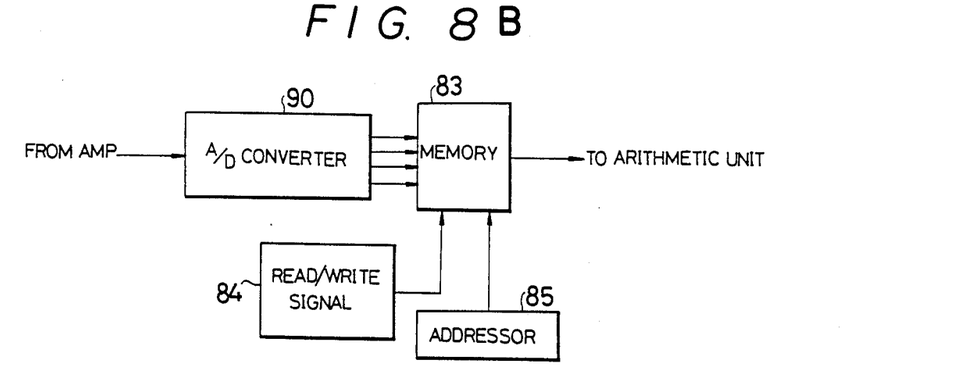

FIGS. 8 (A) and (B) show the circuitry configuration for processing the output of the photomultiplier 27.

In FIG. 8 (A), symbol 80 is a switch for switching the output of the amplifier 28 for amplifying the output of the photomultiplier 27 so as to input it into either counter 81 or 82. The output of counters 81 and 82 is switched by switch 87. The cl ocks used when the counter is counting, in particular the clocks generating the time units when counting the aforesaid flares and cells, are formed by the unit time clock circuit 88. Whenever any measuring period ends, the count values on counters 81 and 82 are initialized by the clear signal circuit 87 by switch 89.

A memory circuit 83 for storing the count values is provided after counters 81 and 82. Writing into and reading out from this memory is controlled by the read/write signal circuit 84. The addresses during reading and writing are controlled by an address specifying circuit 85 which includes an address decoder.

The measured data stored in this memory 83 are processed by the method described above by an arithmetic unit 86 consisting of microprocessors and the like.

In the configuration described above, when a pulse train is input from the photoelectric converter, counters 1 and 2 are switched back and forth in use at definite units of time by the unit time clock circuit 88. For example, when counter 1 is counting, counter 2 transmits the count data to the memory area specified by the address specifying circuit 85. Write signals are output at this time from the read/write signal circuit 84.

After the output of counter 2 has been transmitted to memory, a clear signal is input into counter 2 by the clear signal circuit 87, and counter 2 is cleared. When counter 1 finishes counting its unit of time, the unit time clock circuit 88 now causes counter 2 to begin counting. The aforesaid processing is repeated until the end of the measurement time. When measurement is finished, the arithmetic unit immediately triggers the read/write signal circuit 84 to output a read signal, and the data are output from the memory 83 to the arithmetic unit 86.

On the other hand, FIG. 8 (B) illustrates an example in which a digital conversion circuit is configured with an A/D converter. A configuration such as this is used in cases where the data are output from the photoelectric converter as quantities of voltage or the like.

The analog data output by the photoelectric converter are converted by the A/D converter 90 into digital quantities expressed in terms of step widths of a predetermined number of bits. In the example illustrated, the A/D converter outputs the data in parallel to the memory 83. The reading and writing actions of the memory 83 are controlled by the read/write signal circuit 84 and the address specifying circuit 85, just as in the example shown in FIG. 8 (A).

Configurations such as those mentioned above make it possible to measure flares and cells as described above.

In the embodiments described above, the method illustrated was one in which measurements are performed by inserting and removing a linear polarizer. By using a configuration like that shown in FIG. 9, it is possible to omit the configuration for mechanically inserting and removing the polarizer.

Figure 9:
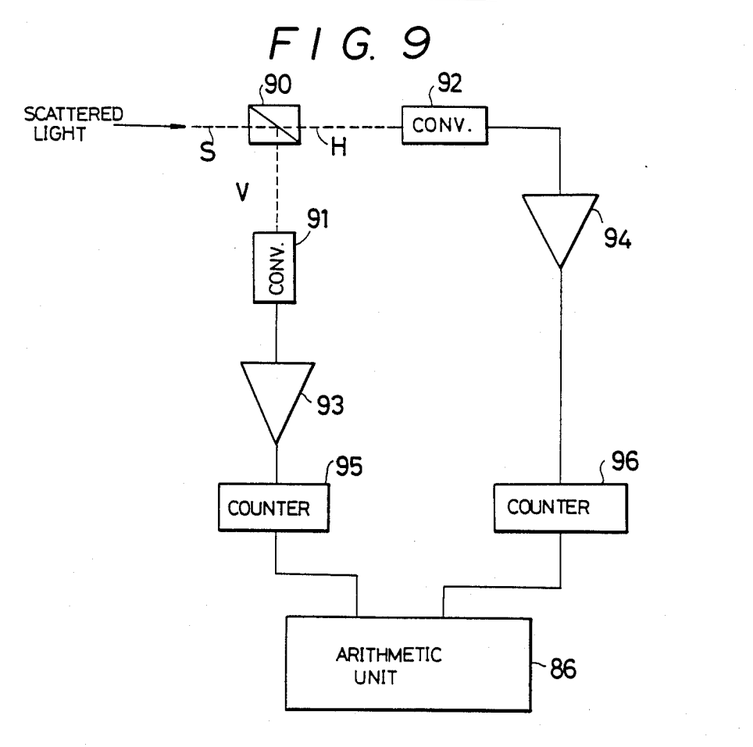
FIG. 9 is an explanatory diagram illustrating a different embodiment of this invention.

Symbol 90 in FIG. 9 represents a polarizing beam splitter. This polarizing beam splitter detects the light S scattered from the patient's eye and outputs vertically polarized components V and horizontally polarized components H. The vertically and horizontally polarized components V and H are each received by separate photoelectric converters 91 and 92 and are converted into electrical signals.

The output of the photoelectric converters 91 and 92 is amplified to a predetermined level by amplifiers 93 and 94 and is input into the counters 95 and 96. Counters 95 and 96, as described above, each detect the photons output from the photoelectric converters 91 and 92 through amplifiers 93 and 94 and count the number of pulses.

Since the vertically and horizontally polarized components are divided by a polarizing beam splitter 97, as mentioned above, the photon counts obtained by the counters 95 and 96 will each reflect the intensities of the vertically and horizontally polarized components in the light components scattered from the patient's eye.

Consequently, if the counts obtained by the counters 95 and 96 are analyzed by the arithmetic unit 86 in accordance with the same standards as described above, it will be possible to detect quantitatively the numbers of flares and cells in the patient's eye.

In the configuration shown in FIG. 9, the cost of manufacturing the apparatus can be reduced since the mechanical configuration for inserting and removing the linear polarizer can be omitted. It also has an added advantage in that the measurements can be made at a higher speed, since the sequence for inserting and removing the linear polarizer can be omitted during measurement.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic measuring method for measuring the step of microparticles in the aqueous chamber of an eye to be examined which is irradiated with a laser beam to detect the scattering characteristics in the aqueous chamber of said eye, comprising the steps of:
   projecting a laser beam with a predetermined wavelength into an aqueous chamber in a given direction;
   receiving light scattered from the aqueous chamber in a direction perpendicular to the given direction through a polarizer which passes only horizontally polarized components;
   receiving light scattered from the aqueous chamber perpendicular to said given direction without a linear polarizer; and
   evaluating the changes between the characteristics of scattered light received with said linear polarizer and scattered light received without the linear polarizer to measure at least one of the number and concentration of microparticles present in said aqueous chamber.

2. A method as set forth in claim 1, wherein said microparticles are plasma proteins or blood corpuscles.

3. A method as set forth in claim 2, wherein said laser beam is scanned when said aqueous chamber contains more blood corpuscles than plasma proteins.

4. A method as set forth in claim 2, wherein said laser beam is fixed when said aqueous chamber contains only plasma proteins.

5. An ophthalmic measuring apparatus for measuring the state of microparticles in the aqueous chamber of an eye to be examined which is irradiated with a laser beam to detect the scattering characteristics in the aqueous chamber of said eye, comprising:
   a laser source for producing a laser beam having a predetermined wavelength;
   means for projecting said laser beam into the aqueous chamber of said eye to be examined in a given direction;
   means for directing light scattered from the aqueous chamber in a direction perpendicular to the given direction and for passing a portion of the light through a polyarizer which passes only horizontally polarized components;
   a photoelectric converter for receiving the polarized and nonpolarized light scattered by said microparticles in said aqueous chamber and for producing analog signals;
   means for converting the analog signals from said photoelectric converter into digital signals; and
   means for counting said digital signals to determine the number of pulses per unit time and evaluating the changes between the scattering characteristics of polarized and non-polarized light to measure one of the number and concentration of the microparticles present in said aqueous chamber.

6. An apparatus as set forth in claim 5, wherein said counting means includes two counters and means for effecting the counting in one of the counters to count the number of pulses while the other counter is connected to said evaluating means to transfer the count thereto for ophthalmic measurement.

7. An apparatus as set forth in claim 5, wherein said converting means is an analog-digital converter.

8. An ophthalmic measuring apparatus for measuring the state of microparticles in the aqueous chamber of an eye to be examined which is irradiated with a laser beam to detect the scattering characteristics in the aqueous chamber of said eye, comprising:
   a laser source for producing a laser beam having a predetermined wavelength;

means for projecting said laser beam into the aqueous chamber of said eye to be examined;

a polarizing beam splitter for dividing the light scattered by said microparticles in said aqueous chamber into vertically and horizontally polarized components;

a first photoelectric converter for receiving said vertically polarized components for conversion into corresponding electrical signals;

a second photoelectric converter for receiving said horizontally polarized components for conversion into corresponding electrical signals;

a first counter for counting the number of pulses in response to said signals from said first photoelectric converter;

a second counter for counting the number of pulses in response to said signals from said second photoelectric converter; and means for receiving said signals from said first and second counters and measuring the number or concentration of the microparticles present in said aqueous chamber for the purpose of ophthalmic evaluation.

* * * * *